US00PP26345P2

(12) United States Plant Patent
Trees

(10) Patent No.: US PP26,345 P2
(45) Date of Patent: Jan. 26, 2016

(54) ***ROSA* PLANT NAMED 'SFROSA151'**

(50) Latin Name: *Rosa hybrida*
Varietal Denomination: SFROSA151

(71) Applicant: Scott C. Trees, Arroyo Grande, CA (US)

(72) Inventor: Scott C. Trees, Arroyo Grande, CA (US)

(73) Assignee: Sunrise Farm Flowers, LLC., Arroyo Grande, CA (US)

( * ) Notice: Subject to any disclaimer, the term of this patent is extended or adjusted under 35 U.S.C. 154(b) by 4 days.

(21) Appl. No.: 14/121,318

(22) Filed: Aug. 19, 2014

(51) Int. Cl.
*A01H 5/02* (2006.01)

(52) U.S. Cl.
USPC ..... Plt./104

(58) Field of Classification Search
USPC ..... Plt./104
CPC ..... A01H 5/0222; A01H 5/0216
See application file for complete search history.

*Primary Examiner* — Kent L Bell
(74) *Attorney, Agent, or Firm* — Penny J. Aguirre

(57) ABSTRACT

A new cultivar of shrub rose plant, 'SFROSA151', that is characterized by its compact and upright plant habit, its flowers that are a saturated yellow color and nearly non-fading, its flowers with 20 to 25 reflexed petals, its mild tea fragrance, its glossy dark green foliage, its cold hardiness at least to U.S.D.A. Zone 6, and its tolerance to resistance to powdery mildew and rust.

2 Drawing Sheets

Botanical classification: *Rosa hybrida.*
Variety denomination: 'SFROSA151'.

BACKGROUND OF THE INVENTION

The present invention relates to a new and distinct cultivar of *Rosa hybrida*. The new cultivar will be referred to hereafter by its cultivar name, 'SFROSA151'. 'SFROSA151' is a new cultivar of shrub rose grown for use as a landscape shrub.

The new cultivar of shrub rose is a selection from a controlled breeding program conducted by the Inventor in Arroyo Grande, Calif. with an objective to create new shrub rose cultivars with disease resistance, ever blooming habits, unique brightly colored flowers that can be readily propagated on their own roots.

The new cultivar of shrub rose, 'SFROSA151', was selected by the Inventor from amongst seedlings derived from a cross made in July of 2010 between plants of the cultivar, 'WEKvossutono' (U.S. Plant Pat. No. 18,473) as both the female and male parent. 'SFROSA151' was selected as a single unique plant in May of 2011.

Asexual propagation of the new cultivar was first accomplished by stem cuttings in Arroyo Grande, Calif. in August of 2011 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SFROSA151' as a new and unique cultivar of shrub rose.

1. 'SFROSA151' exhibits a compact, upright plant habit.
2. 'SFROSA151' exhibits flowers that are a saturated yellow color and nearly non-fading.
3. 'SFROSA151' exhibits semi-double flowers with 20 to 25 reflexed petals.

4. 'SFROSA151' exhibits a mild tea fragrance.
5. 'SFROSA151' exhibits glossy dark green foliage.
6. 'SFROSA151' exhibits cold hardiness at least to U.S.D.A. Zone 6.
7. 'SFROSA151' exhibits tolerance to resistance to powdery mildew and rust.

'SFROSA151' can be distinguished from plants of its parent, 'WEKvossutono', which differs from 'SFROSA151' in having flowers that are light orange-yellow in color, in having double flowers with more than 35 petals, in having a more branched plant habit, and in having foliage that is light green in color. 'SFROSA151' can be most closely compared to plants of the shrub rose cultivars 'SPRoimpress' (U.S. Plant Pat. No. 21,708) and 'WEKyesir' (U.S. Plant Pat. No. 21,989). 'SPRoimpress' differs from 'SFROSA151' in having smaller flowers that are borne in clusters and lack fragrance and in having a taller more upright plant habit. 'WEKyesir' is similar to 'SFROSA151' in having flowers that are bright yellow in color and in having an upright plant habit. 'WEKyesir' differs from 'SFROSA151' in having flowers that are smaller in diameter and often borne in clusters, in growing taller in one season, and in having a stronger fragrance.

BRIEF DESCRIPTION OF THE DRAWINGS

The accompanying colored photographs illustrate the overall appearance and distinct characteristics of the new shrub rose. The photographs were taken of a one year-old plant as grown outdoors in a one-gallon container in Arroyo Grande, Calif.

The photograph in FIG. 1 provides a side view of the plant habit of 'SFROSA151'.

Figure 1:
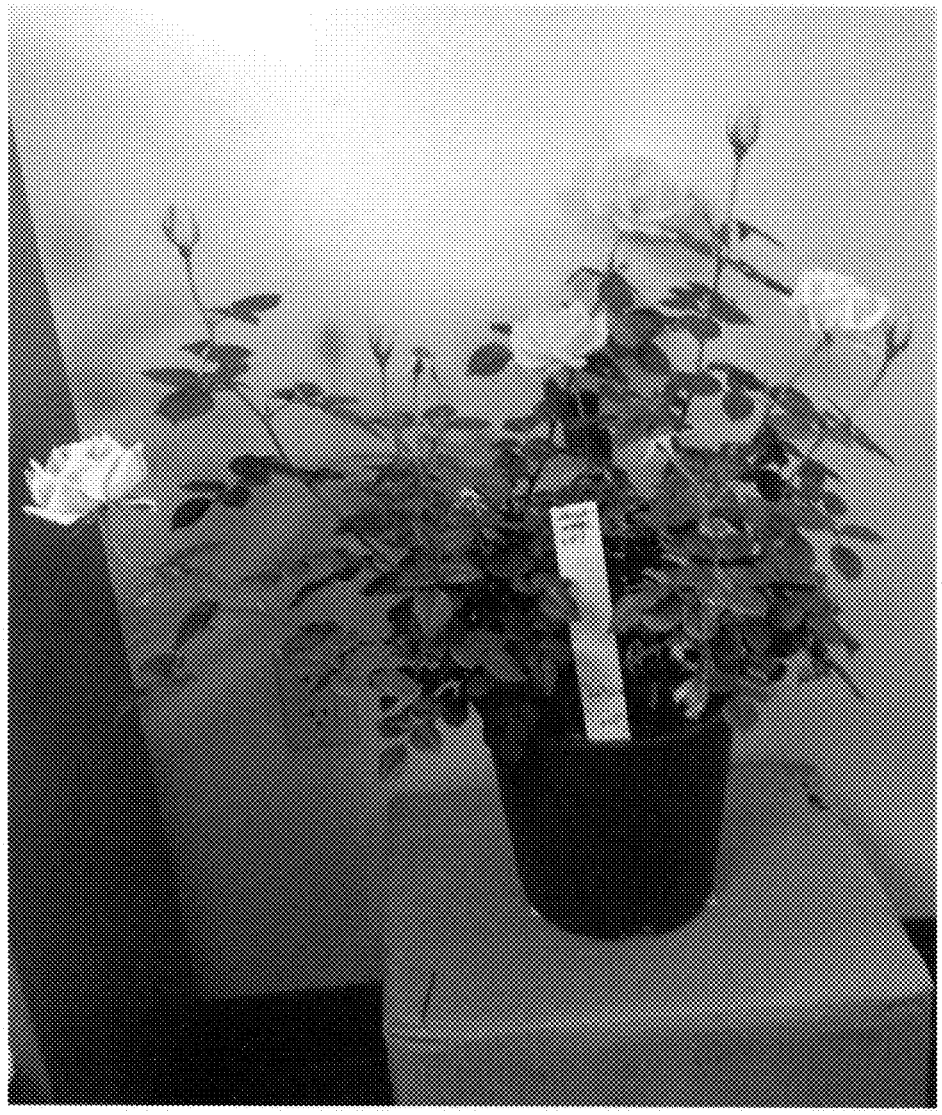
Figure 2:
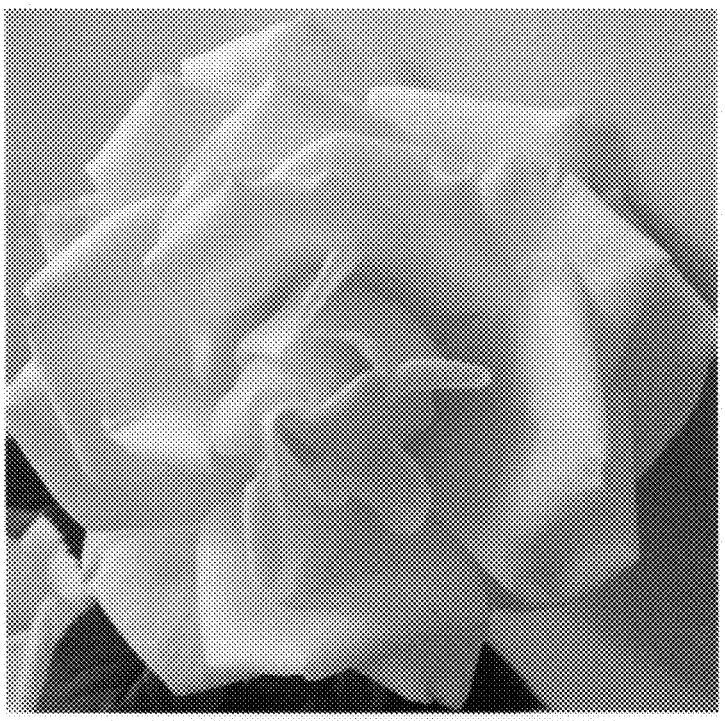

The photograph in FIG. 2 provides a close-up view of a flower of 'SFROSA151'.

Figure 3:
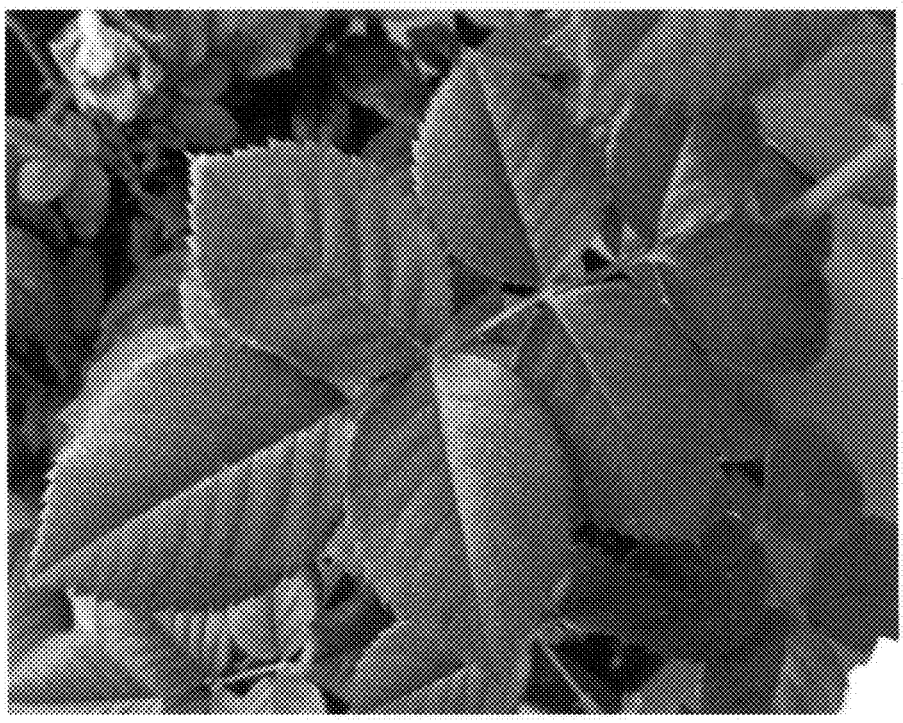

The photograph in FIG. 3 provides a close-up view of a leaf of 'SFROSA151'.

The colors in the photographs are as close as possible with the photographic and printing technology utilized and the color values cited in the detailed botanical description accurately describe the colors of the new shrub rose.

DETAILED BOTANICAL DESCRIPTION

The following is a detailed description of nine month-old plants the new cultivar as grown outdoors in 1-quart containers in Arroyo Grande, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Continuous bloom in California from June to first frost in the Midwestern, northeastern, and southeastern areas of the United States.

*Plant type.*—Deciduous shrub.

*Plant habit.*—Upright and compact.

*Height and spread.*—Reaches 60 cm height and width in one season in the garden.

*Cold hardiness.*—At least to U.S.D.A. Zone 6.

*Diseases and pests.*—Has shown tolerance to powdery mildew and rust.

*Propagation.*—Stem cuttings.

*Growth rate.*—Slow to moderate.

Branch description:

*Stem color.*—Young; 144B suffused with 179A maturing; 144A to 144B, mature wood; ridges of 177B.

*Stem surface.*—Young; glabrous, mature; very slightly glaucous, adult wood; finely barked.

*Branching.*—1 to 3 lateral branches per main stem, 2 main stems per 1-quart container.

*Stem size.*—Average of 5 mm in width, up to 20 cm in length.

*Thorns.*—Triangular shape, aspect slightly downward, base oval, average of 5 mm in length with a base 4.5 mm in length and 2 mm in width, 144B, upper surface suffused with 179A in color, an average of 25 in number per 20 cm length stem.

Foliage description:

*Leaves.*—Compound, division is odd-pinnate, arrangement is alternate, average of 8 cm in length and 5.5 cm in width, internode length is an average of 1.5 cm.

*Leaflets.*—7, occasionally 5, average of 2.5 cm in length and 2 cm in width, ovate to round in shape, rounded base, acute apex, serrate margins, color; emerging leaves upper surface; 144A to 144B with 183A at the margins, emerging leaves lower surface; 144A lightly suffused with 183A at the margins, young leaves upper surface; 137B thinly margined with 183A, young leaves lower surface; 138B, mature leaves upper surface; 137A, mature leaves lower surface; 138B, pinnately veined (not conspicuous), surface glabrous and glossy on upper surface and glabrous and dull on lower surface.

*Rachis.*—Average of 4.5 cm in length and 1 mm in diameter, color; upper surface 144A suffused with 183A and lower surface 144B, rounded in shape with a center groove on upper surface, smooth upper and lower surface with a few sparse long hairs on upper surface.

*Stipules.*—Aspect outward, adnate to petiole, free apex acute in shape, average of 1.1 cm in length and 1.5 mm in width, color upper and lower surface; 144A and suffused with 183A, glabrous upper and lower surface, finely serrate margin.

*Petioles and petiolules.*—Petioles; an average of 1 cm in length and 2 mm in diameter, petiolules; an average of 1 mm in length and 1 mm in diameter, petioles and petiolules; color of mature leaves upper surface; 144A suffused with 183A, color of mature leaves lower surface; 144B, upper and lower surfaces are glabrous.

Inflorescence description:

*Inflorescence type.*—Solitary at terminus and upper nodes of lateral branch.

*Flower number.*—1 to 2 per lateral stem, repeats bloom throughout the growing season.

*Flower fragrance.*—Mild tea scent.

*Flower longevity.*—5 to 8 days, depending on temperature and sunlight exposure.

*Flower type.*—Semi-double, rosette in form.

*Flower size.*—Average of 3.5 cm in depth and 4.5 cm in diameter.

*Peduncles.*—Round in shape, average of 4.9 cm in length and 3 cm in diameter, 144A to 144B in color, surface satiny and moderately covered with small prickles; 1 mm in length and 0.3 mm in width 196B in color.

*Bracts.*—2, at base of peduncle, ovate in shape with acute apex, truncate base, margin smooth, an average of 6 mm in length and 3 mm in width, 144A to 144B on upper and lower surface, both surfaces are glabrous.

*Flower buds.*—Ovate in shape, an average of 3 cm in length and 2 cm in width prior to opening, color; 7A with sepal portion a blend of 144A and 137B.

*Sepals.*—5, lanceolate to elliptic in shape, margin entire, color of upper surface; a blend of 143A and 144A, color of lower surface; a blend of 144A to 144A lightly suffused with 183C, average of 3.8 cm in length and 9 mm in width, leaflike apex, truncate base, reflexed to stem on mature flowers, covered with downy hairs NN155 in color on upper surface, glabrous and scaberulose on lower surface.

*Petals.*—An average of 23 per flower (including 3 to 4 petaloid stamens), drop readily and cleanly, obcordate to rounded in shape, upper and lower surface glabrous, margin entire and very slightly undulating, base broadly cuneate, apex is rounded with a slight mucronate tip, up to 3 cm in length and width, color of opening and fully open flowers upper and lower surface; 7A, fading flowers upper and lower surface; 7C (barely fading).

*Hypanthium.*—Average of 9 mm in length and 7 mm in diameter when flower is fully open, cup shaped, glabrous and shiny surface, 144A in color.

*Pistils.*—Average of 36, stigma is an average of 2 mm in diameter and 151D in color, style is an average of 4 mm in length and 154D in color, ovaries are oblong in shape, 3 mm in length, 2 mm in width and 150D in color with a pubescent surface.

*Stamens.*—Average of 70, filaments are about 7 mm in length and 13A in color, anthers are an average of 2 mm in length, and an average of 1.5 mm in width and 13A in color, pollen is moderate in quantity and 22A in color.

*Hips*.—Rarely produced, plants are highly sterile, when produced they are globose in shape with a flattened apex, an average of 2 cm in width and 1.7 cm in height, color is a blend of 138A and 145A with some tints of 22A and 178A, apex is N186C, surface is dull.

It is claimed:

1. A new and distinct cultivar of *Rosa* plant named 'SFROSA151' as herein illustrated and described.

* * * * *